United States Patent [19]

Hildon et al.

[11] 4,160,778

[45] Jul. 10, 1979

[54] EPOXIDATION

[75] Inventors: Anthony M. Hildon, Tattenhall; Thomas D. Manly, Runcorn; Alan J. Jaggers, Rainhill, all of England

[73] Assignee: Propylox a Society Anonyme, Brussels, Belgium

[21] Appl. No.: 873,523

[22] Filed: Jan. 30, 1978

[30] Foreign Application Priority Data

Feb. 26, 1977 [GB] United Kingdom .................. 8246/77

[51] Int. Cl.$^2$ : .......................................... C07C 179/10
[52] U.S. Cl. ............................................... 260/502 R
[58] Field of Search ........................ 260/502 R, 502 A

[56] References Cited

U.S. PATENT DOCUMENTS 3,140,312  7/1964  Kurhajec et al. ................ 260/502 R

FOREIGN PATENT DOCUMENTS 2602776  5/1976  Fed. Rep. of Germany ...... 260/502 R
1425077  2/1976  United Kingdom ................ 260/502 R

*Primary Examiner*—Werren B. Lone
*Attorney, Agent, or Firm*—Larson, Taylor and Hinds

[57] ABSTRACT

The invention provides a continuous process for the preparation of a peracid which comprises reacting hydrogen peroxide with a carboxylic acid in an aqueous medium containing a mineral acid, and extracting the peracid thus formed into an organic phase comprising an organic solvent so as to produce an aqueous solution comprising sulphuric acid and water and an organic solution comprising peracid and organic solvent, wherein the hydrogen peroxide is added to the reaction mixture in a plurality of stages, thereby to limit the concentration of hydrogen peroxide at any location. Preferably the reaction and extraction are effected simultaneously.

9 Claims, 1 Drawing Figure

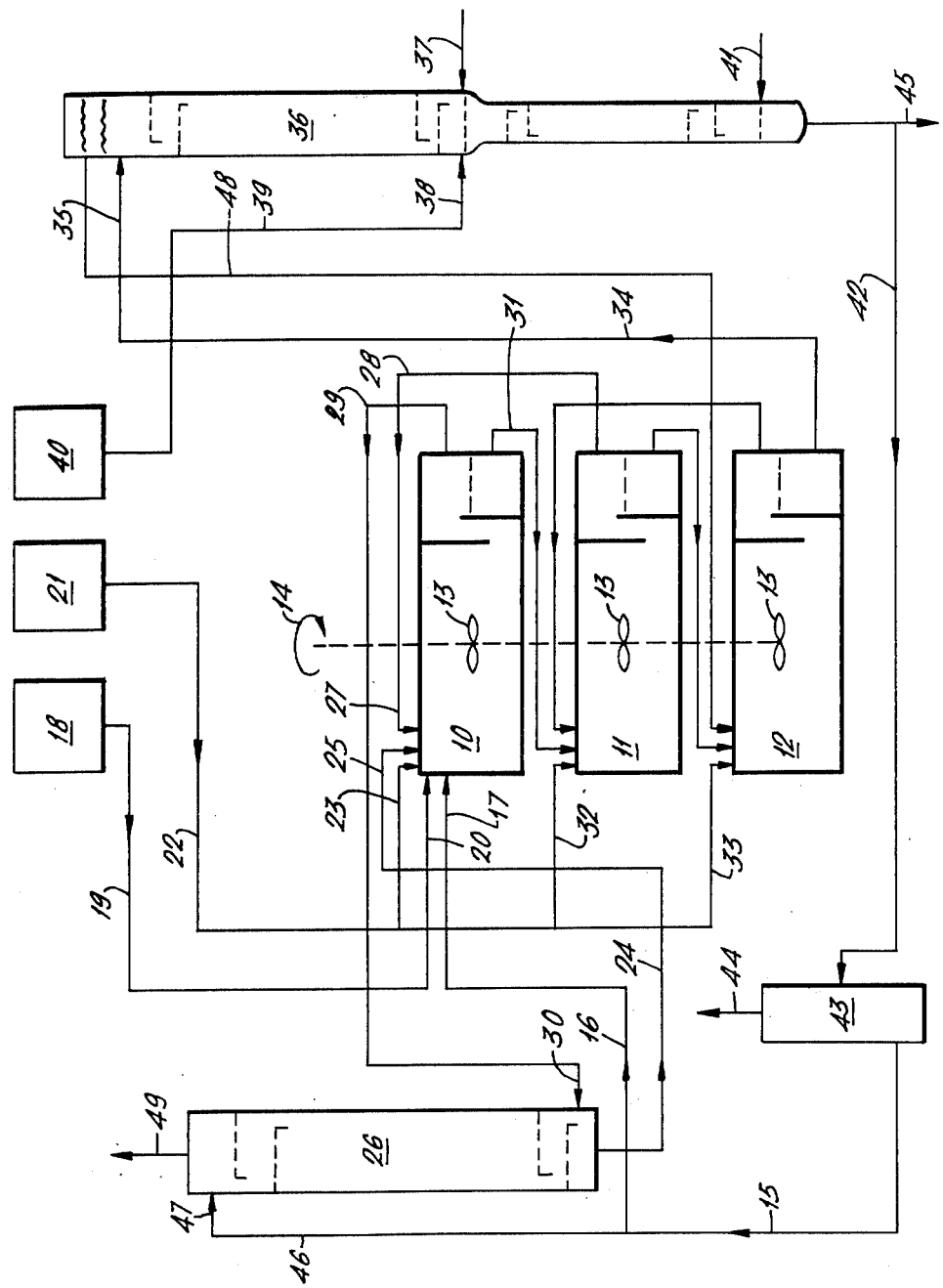

EPOXIDATION

BACKGROUND TO THE INVENTION

The present invention relates to the preparation of peracids (by which we mean herein peroxycarboxylic acids). The use of such peracids in the epoxidation of alkenes, especially lower alkenes, is well known.

DESCRIPTION OF THE PRIOR ART

The preparation of peracids by the reaction of a carboxylic acid with hydrogen peroxide in an aqueous medium is well known. It is also known that such peracids can be extracted into organic solvents. Finally it is known that peracids can be used to make oxiranes. One process for the preparation of peracids and their use to make oxiranes is disclosed in DOS No. 26 02 776. An alternative process is disclosed in BP No. 1 425 077.

SUMMARY OF THE INVENTION

It is an object of the present invention to provide a novel continuous process for the preparation of a peracid.

Accordingly the present invention provides a continuous process for the preparation of a peracid which comprises reacting hydrogen peroxide with a carboxylic acid in an aqueous medium containing a mineral acid, and extracting the peracid thus formed into an organic phase comprising an organic solvent so as to produce an aqueous solution comprising sulphuric acid and water and an organic solution comprising peracid and organic solvent, wherein the hydrogen peroxide is added to the reaction mixture in a plurality of stages, thereby to limit the concentration of hydrogen peroxide at any location.

Preferably, as described in the said DOS, the reaction and extraction are effected simultaneously.

Thus, according to yet another aspect of the invention a continuous process for the production of a peracid comprises a. providing an aqueous phase comprising sulphuric acid, hydrogen peroxide and water;
b. providing an organic phase comprising a carboxylic acid and an organic solvent;
c. contacting said aqueous and organic phases countercurrently to effect extraction and produce an aqueous solution comprising sulphuric acid and water and an organic solution comprising peracid and organic solvent, wherein the hydrogen peroxide is added to the aqueous phase in a plurality of stages, thereby to limit the maximum concentration of hydrogen peroxide at any location.

COMPARISON WITH THE PRIOR ART

It is now convenient to compare the present process with the prior art and specifically with the said DOS, from a technical standpoint, upon the assumption that the carboxylic acid is propionic acid and the solvent is propylene dichloride.

It is well known that mixtures of hydrogen peroxide, water and an organic material such as a carboxylic acid may be potentially explosive, the degree of risk depending upon the relative proportions of the three components. Thus, it may be undesirable to react together concentrated hydrogen peroxide and carboxylic acid in order to make a peracid and then extract the product peracid into an organic phase, since, in such a system, the optimum proportions of reagents will almost certainly be those which must be considered hazardous.

The procedure disclosed in the said DOS avoids some of the problems since the carboxylic acid is supplied to the reaction system in solution in the organic solvent and in countercurrent to the hydrogen peroxide. In such a system, at the end of the extraction stage, where the hydrogen peroxide is introduced, the concentration of hydrogen peroxide is at its highest, but it is inherently unlikely that there would be any significant proportion of carboxylic acid present in the aqueous phase which might make an explosion likely. It must of course be understood that in considering a reaction which takes place in a continuous manner in a countercurrent exchange device such as a column, it is the concentrations at any one location in the column which must be considered and not the average concentration throughout the column. Moreover it is possible to operate a process of this type in such a way as to get either substantially complete conversion of the carboxylic acid to peracid or substantially complete utilisation of the hydrogen peroxide. The latter choice is usually preferred, as unreacted carboxylic acid can be more easily recycled. To achieve substantially complete reaction of hydrogen peroxide it is preferable to operate with a small excess of carboxylic acid. It will be apparent that for overall efficiency of the operation the amount of water present in the system should be reduced, but not to the extent that, in those areas of the extraction system where the hydrogen peroxide concentration is high and unreacted carboxylic acid is also present, this could lead to risk of explosion.

It will of course be understood that the presence of mineral acid, desirably sulphuric acid, is essential in order effectively to catalyse the reaction. In a carboxylic acid — $H_2O_2$—$H_2SO_4$—$H_2O$ system, the $H_2SO_4$, from the point of view of the explosive properties of the mixture, can be considered as having substantially the same effect as water, and any by-product peroxides found (e.g. Caro's Acid $H_2SO_5$) can be considered as equivalent $H_2O_2$.

In practising the procedure of the present invention, the effect is to limit the maximum hydrogen peroxide concentration in the aqueous phase and reduce the risk of explosion. More specifically, we restrict the maximum concentration of hydrogen peroxide at any location within the extraction device, since at each location the bulk of the $H_2O_2$ supplied is rapidly converted to peracid which is extracted into the organic phase.

GENERALISED DESCRIPTION

Any form of apparatus suitable for countercurrent extraction is suitable and in the said DOS the use of an extraction column was described. It is possible to employ as the extraction device two or more mixer-settlers suitably arranged so as to achieve a countercurrent effect. It is also possible to employ a combination of one or more columns with one or more mixer-settlers, and until now there has been no reason why any one of these arrangements should be particularly preferred.

More specifically in the said DOS, although the use of mixer-settlers or a combination was contemplated, the specific description related to a 3-section extraction column to which hydrogen peroxide was supplied at the top of the centre section with the upper section functioning as an acid back-wash. Propionic acid in organic solution was supplied to the lower part of the centre section with the lower section of the extraction column constituting a stripper section. In the now preferred arrangement the said three-section extraction column is replaced by a back-wash column, a battery of mixer-settlers, and an extraction column, these mixer-settlers constituting in effect the upper portion of the centre section of the original system. The introduction of hydrogen peroxide into the system is preferably conducted in the mixer-settlers where very efficient mixing takes place, thereby to eliminate the risk of localised high concentrations of hydrogen peroxide which is always possible in column operation. It should be made clear that the invention is not limited to the use of mixer-settlers. Normal, stirred, pulsed or other columns can be used.

SELECTION OF THE CARBOXYLIC ACID

As used herein, the term "carboxylic acid" has its normal meaning but it is necessary to emphasise that in practising the invention a proper selection of the "carboxylic acid" and "organic solvent" is desirable in order to provide optimum efficiencies. However with the guide lines given herein such selection is within the ability of one skilled in the art. It is clearly necessary to select a carboxylic acid such that it and the resulting peracid are sufficiently soluble in water to permit the reaction to take place and are also soluble in the organic solvent. Moreover the carboxylic acid and peracid should not undergo undesirable side reactions. For these reasons we prefer to use unsubstituted monocarboxylic acids having at least two but less than six carbon atoms.

The preferred carboxylic acids are acetic and propionic acids.

SELECTION OF THE SOLVENT

The process to be described in detail is one in which the extraction into the organic phase takes place simultaneously with the reaction to form the peracid, but substantially the same criteria apply to separate reaction and extraction stages.

The prime function of the organic solvent is to provide a discrete organic phase in which the carboxylic acid and peracid are soluble. Additional desirable criteria for the organic solvent are a low solvent power for water, a low solubility in aqueous sulphuric acid and non-reactivity under the conditions of the reaction in the presence of the other reactants. It will be understood that although various solvents are listed herein, the selection of a solvent for practical use must depend on the precise process and reactants, and on the end use for the peracid.

The solvent may be a halogenated, e.g. fluorinated or chlorinated, aliphatic, cycloaliphatic or aromatic hydrocarbon for example:

dichloromethane, trichloromethane, tetrachloromethane,
chloroethane, 1,1-dichloroethane, 1,2-dichloroethane,
1,1,1-trichloroethane, 1,1,2-trichlorethane,
1,1,1,2-tetrachloroethane, 1,1,2,2-tetrachloroethane,
1-chloropropane, 2-chloropropane, 1,1-dichloropropane,
1,2-dichloropropane, 1,3-dichloropropane,
2,2-dichloropropane, 1,1,1-trichloropropane,
1,1,2-trichloropropane, 1,1,3-trichloropropane,
1,2,2-trichloropropane, 1,2,3-trichloropropane,
tetrachloropropanes, or chloro-substituted butanes, pentanes or hexanes, cyclohexyl chloride or chlorobenzene.

Chlorinated hydrocarbons, although normally considered very inert, may give rise to chloride species, which in the presence of water and/or sulphuric acid can be very corrosive. It may therefore be desirable to select the solvent from among the non-chlorinated hydrocarbons, such as aliphatic hydrocarbons, cycloaliphatic hydrocarbons, aromatic hydrocarbons and alkyl-aryl hydrocarbons for example:

decane, heptane, cycloheptane, benzene, toluene or xylene.

Other solvents, known generally in the art of peracids may be used.

A solvent mixture can be used, for example that known as petroleum ether which is a mixture of aliphatic hydrocarbons.

It is not necessary that the organic solvent should be a saturated compound provided that any unsaturation is not epoxidisable under the conditions of the process.

Of all the solvents listed herein, the most preferred are propylene dichloride and benzene.

PRODUCTION OF PERACID

Before describing the plant of the present invention it is convenient to describe, in general terms, the reaction itself.

In the reaction an aqueous phase, comprising sulphuric acid, hydrogen peroxide and water, and an organic phase, comprising carboxylic acid and organic solvent, are passed to the countercurrent extraction apparatus.

The components will partition between the two phases and, in the aqueous phase, the reaction of hydrogen peroxide with carboxylic acid to give peracid will be catalysed by the sulphuric acid. This reaction is normally slow to reach equilibrium but is accelerated by the extraction of the peracid into the organic phase.

In addition to its function as catalyst, the sulphuric acid also has the function of adjusting the specific gravity of the aqueous phase to assist separation of the phases. The relative specific gravity of the organic and aqueous phases will determine their direction of movement in countercurrent operation in a column. However care should be taken, as is known, that the concentration of the sulphuric acid is maintained so as to be sufficient for catalysis but insufficient to cause degradation of any of the organic components by dehydration, etc.

The aqueous solution removed from the extraction device has, in effect, had some or all of its hydrogen peroxide replaced by water. It is therefore desirably concentrated by the removal of water and recycled after addition of hydrogen peroxide.

PRODUCTION OF PERACID — GENERAL CONDITIONS

Dealing with this part of the invention in more detail and as applied specifically to the preparation of perpropionic acid, using propylene dichloride as the organic solvent, an aqueous phase is supplied to the extraction device and comprises sulphuric acid, hydrogen peroxide and water. The proportion of sulphuric acid is desirably between 30% and 60% by weight and is preferably approximately 40% by weight. Conveniently for operating reasons the sulphuric acid is derived from 75% by weight sulphuric acid solution in water which forms a feedback from the purification stages which will be described hereinafter, together with make-up acid.

The hydrogen peroxide is, in accordance with the invention, added into the aqueous phase in a number of locations. The total amount added is conveniently between 10% and 35% by weight of the aqueous phase and in practice 29% is very satisfactory. This hydrogen peroxide is very conveniently supplied as approximately 70% by weight solution in water.

Water makes up the third component of the aqueous phase and its proportions can readily be found by difference.

The organic phase is fed into the extraction device to pass in countercurrent with the aqueous phase and comprises, for the production of perpropionic acid, a solution of propionic acid in propylene dichloride. The concentration of the propionic acid is preferably between 15% and 30% of the organic phase and desirably 20% by weight.

The relative volumes of the aqueous and organic phases passing through the apparatus in unit time and their concentrations together set the ratio between hydrogen peroxide and propionic acid. This ratio may be from 1:0.5 to 1:4 by moles but is conveniently about 1:1.4, the theoretical ratio being 1:1.

It may be convenient to carry out a further extraction of the aqueous phase leaving the extraction device using fresh organic solvent in order to extract substantially all of both propionic acid and perpropionic acid from the aqueous effluent. It may also be convenient to effect a back-wash operation on the organic phase in order to remove dissolved hydrogen peroxide. This latter can be effected by dividing the aqueous feed to the device into two portions, one being primarily dilute sulphuric acid and the other primarily hydrogen peroxide, and introducing these two portions at spaced locations in the device.

The reaction proceeds naturally at a satisfactory rate so that operation at natural temperatures is satisfactory. Natural temperature is to some extent dependent on a scale effect since only little heat is evolved on mixing and reaction. Since the reaction is not markedly temperature sensitive no special steps are needed and a temperature of 20°-25° C. is satisfactory.

As a guide to the selection of a reactant/solvent system for the production of the peracid, reference should be made to Table 1 which shows some relevant data.

TABLE I

|  | pK × 10⁵ | Boiling Point °C. | Density g/cc | Solubility in water |
|---|---|---|---|---|
| Carboxylic Acids |  |  |  |  |
| formic | 17.7 | 101 | 1.22 | ∞ |
| acetic | 1.8 | 118 | 1.04 | ∞ |
| propionic | 1.3 | 141 | 0.99 | ∞ |
| n.butyric | 1.5 | 163 | 0.96 | ∞ |
| caproic | 1.4 | 205 | 0.93 | δ |
| n.heptoic | 1.3 | 223 | 0.92 | δ |
| chloracetic | 140 | 189 | 1.28 | v |
| α-chlorpropionic | 147 | 186 | 1.28 | ∞ |
| β-chlorpropionic | 10 | 204 | — | s |
| Solvents |  |  |  |  |
| chloroethane |  | 13.1 | 0.90 | δ |
| tetrachloroethane |  | 146 | 1.60 | δ |
| propylene dichloride |  | 96 | 1.16 | δ |
| chlorobenzene |  | 132 | 1.11 | i |
| cyclohexylchloride |  | 142 | 1.00 | i |
| trichlorethylene |  | 87 | 1.46 | δ |
| tetrachlorethylene |  | 121 | 1.62 | i |
| decane |  | 174 | 0.73 | i |

TABLE I-continued

|  | pK × 10⁵ | Boiling Point °C. | Density g/cc | Solubility in water |
|---|---|---|---|---|
| heptane |  | 98 | 0.68 | i |
| cyclohexane |  | 81 | 0.78 | i |
| benzene |  | 80.1 | 0.88 | δ |
| toluene |  | 110 | 0.87 | i |
| ethylacetate |  | 77 | 0.90 | s |
| ethyl propionate |  | 99 | 0.89 | δ |
| nitrobenzene |  | 211 | 1.20 | δ |
| di n-propyl ether |  | 91 | 0.74 | δ |
| petroleum ether |  | 80–100 | 0.8 | i |

Notes to Table I
1. The K figures are for aqueous solution at 25° C.
2. The symbols for solubility are taken from Handbook of Chemistry and Physics; The Chemical Rubber Co; 46th Ed.

In order that the present invention may be more readily understood one embodiment of the same will now be described with reference to the accompanying drawing which is a flow-sheet showing the production of perpropionic acid.

The plant illustrated schematically in the drawings is very similar to the plant described in the said DOS. In consequence therefore only the minimum is shown in the drawing that is necessary to illustrate this invention. Thus it is to be assumed that the plant shown is a part of a larger plant such as that shown in FIG. 1 of the said DOS. More generally the perpropionic acid generated in the plant illustrated in the drawing is consumed and there is an input of propionic acid in solution in an organic solvent, specifically propylene dichloride. This input may be a feed-back stream. Thus in the plant for producing the perpropionic acid there is a circulating aqueous stream containing acid and flowing generally counter to the organic stream containing the propionic and perpropionic acids.

Referring now to the drawing, it will be seen that the plant comprises a battery of three mixer-settlers 10, 11, and 12, each having a paddle 13 or other mechanical mixing device driven by a motor schematically indicated at 14. More, or fewer, mixer-settlers could be used if desired.

A recycle flow of acid takes place in a line 15 and a part of this flow is diverted via a line 16 to an input 17 to the first mixer-settler 10 which may also be supplied with fresh acid from a fresh acid tank 18 via a line 19 leading to an inlet 20. Fresh acid may also be charged as make-up at other points in the acid circuit if preferred. The mixer-settler 10 is also supplied with hydrogen peroxide from a tank 21 via a line 22 which leads to an inlet 23 to the mixer-settler. The mixer-settler 10 is also supplied with further relatively dilute acid through a line 24 leading to an inlet 25, this dilute acid being derived from the base of a back-wash column 26. The mixer-settler 10 has a further inlet 27 which is supplied through a line 28 from the upper settling compartment in the mixer-settler 11.

It should be mentioned that the mixer-settlers depicted herein are of the type having inlets into a main part in which is located the stirrer or paddle, the mixed phases flowing from the main part via a baffle arrangement into a settling compartment where they stratify into an upper organic phase and a lower aqueous phase (using the solvents of this particular system). The arrangement of the battery is such that the organic phase from the middle mixer-settler 11 is pumped (by means not shown) up to the mixer-settler 10 whilst the aqueous phase is pumped down to the mixer-settler 12. It will be understood, however, that the use of pumps is not essential, as some or all of the pumps can be replaced by gravity flow.

The organic phase is taken from the settling compartment of the mixer-settler 10 by a line 29 to an inlet 30 at the base of the back-wash column 26. The aqueous phase from the mixer-settler 10 is taken by a line 31 to the input of the mixer-settler 11 where it is mixed with the organic phase from the mixer-settler 12. The mixer-settler 11 is also supplied with further hydrogen peroxide from the line 22 by an inlet 32.

The mixer-settler 12 is also supplied with further hydrogen peroxide from the line 22 through an inlet 33 and also with aqueous phase from the mixer-settler 11. The total additions of hydrogen peroxide to the system may be made in equal or unequal parts at the several points of addition (inlets 23, 32 and 33 to mixer-settlers 10, 11 and 12). A preferred procedure is to add, at each point, such a quantity of hydrogen peroxide as will produce, at that point and prior to reaction with carboxylic acid, the maximum concentration that is considered to constitute a non-explosive composition, having regard, of course, to the concentrations of other reagents present.

The aqueous phase from the mixer-settler 12 is taken by a line 34 to an inlet 35 at the top of an extraction column 36 and flows downwardly therethrough. The rate of flow of the phases, the dimensions of the column and the dimensions and spacings of the plates are desirably such that the phases substantially reach chemical as well as physical equilibrium at each stage and there is a negligably small amount of free hydrogen peroxide left in the aqueous phase when it reaches the point of the column 36, defined by an inlet 37, which is an inlet for a solution of propionic acid in propylene dichloride, e.g. a recycle stream from an epoxidation reaction. Fresh or make-up propionic acid in propylene dichloride may also be supplied to an inlet 38 by a line 39 from a tank 40, the inlet 38 being at substantially the same level as the inlet 37.

The lower part of the column 36 (i.e. below inlet 37) functions as a stripper section to remove unreacted carboxylic acid from the aqueous phase and is supplied, through a bottom inlet 41, with propylene dichloride containing substantially no propionic acid, this propylene dichloride also coming from a recycle stream. The aqueous phase (comprising essentially only sulphuric acid and water) which has travelled down the extraction column 36 to the bottom is taken through a line 42 to a concentrator 43 where it is concentrated, the water resulting from the reaction of hydrogen peroxide with propionic acid together with the water entrained in the aqueous hydrogen peroxide solution fed to the system, being removed, e.g. by distillation, through a line 44. A portion of the acid stream may be purged to waste via a line 45 prior to the concentrator 43 in order to remove soluble by-product impurities from the system, which would otherwise accumulate. The concentrated acid then forms the acid in line 15 above described. The acid stream in the line 15, in addition to going to the line 16, also goes via a line 46 to an inlet 47 at the top of the back-wash column 26.

The organic phase reaching the top of the column 36 comprises propionic acid in propylene dichloride together with some perpropionic acid and this is taken by a line 48 to form the input to the mixer-settler 12. As this organic phase moves upwardly through the mixer-settlers to exit from the mixer-settler 10 by the line 29, substantially all of the propionic acid is reacted with hydrogen peroxide to give perpropionic acid. The introduction of the hydrogen peroxide into the reaction in three stages, using mixer-settlers, ensures that there is no local over-concentration of hydrogen peroxide. It will be recalled that this is important since there is always a risk of explosion in hydrogen peroxide/water/organic compound systems if the concentrations of the various components lie in the well known dangerous areas. The use of a two-phase system reduces the risks very enormously, since it is really only the aqueous phase that is likely to be explosive (since this is where high concentrations of hydrogen peroxide are required to drive the desired reaction) and the majority of the organic compound is extracted into the organic phase, and as a further safety measure the hydrogen peroxide is introduced at different locations in the continuous reaction system. The concentration of peracid in the organic phase is limited to a safe maximum by the use of a suitable excess of solvent.

The organic phase from the line 29 passes to the back-wash column 26 and leaves the top of this column through an output line 49.

The product of the plant, appearing in line 49, is a solution of perpropionic acid in propylene dichloride. If this solution is to be used in an epoxidation process then desirably the epoxidation provides a recycle of propionic acid in propylene dichloride entering via line 37 and, preferably, a further recycle of substantially pure solvent entering via line 41, as described in the said DOS.

It will be seen that the adaption of this method of feeding hydrogen peroxide to the system largely removes the limitation on the concentration of hydrogen peroxide in the aqueous phase due to hazard considerations so that it becomes practicable and safe to use higher concentrations of hydrogen peroxide feed (so accelerating the rate of reaction) or higher quantities of hydrogen peroxide feed (so increasing the throughput of the plant with better conversion of carboxylic acid to peracid) without the increased risk of explosion that would otherwise arise.

We claim:

1. In a continuous process for the preparation of a peracid which comprises reacting, in a reaction zone, hydrogen peroxide with an unsubstituted monocarboxylic acid having from 2 to 6 carbon atoms in an aqueous medium containing sulfuric acid to form a percarboxylic acid, and extracting the percarboxylic acid thus formed into an organic phase comprising an organic solvent, thereby to produce an aqueous solution comprising sulphuric acid and water and an organic solution comprising percarboxylic acid and organic solvent, the improvement wherein the hydrogen peroxide is added to the reaction mixture at a plurality of locations in the reaction zone, thereby to limit the concentration of hydrogen peroxide at any location in the reaction zone.

2. The process of claim 1, wherein the reaction and extraction are effected simultaneously.

3. In a continuous process for the preparation of a peracid, which comprises:
   a. providing an aqueous phase comprising sulphuric acid, hydrogen peroxide and water;
   b. providing an organic phase comprising an unsubstituted monocarboxylic acid having from 2 to 6 carbon atoms and an organic solvent;
   c. contacting said aqueous and organic phases countercurrently in a countercurrent reaction zone to effect reaction and extraction and produce an aqueous solution comprising sulphuric acid and water and an organic solution comprising peracid and organic solvent, the improvement wherein the hydrogen peroxide is added to the aqueous phase at a plurality of locations in the countercurrent reaction zone, thereby to limit the maximum concentration of hydrogen peroxide at any location in the countercurrent reaction zone.

4. The process of claim 3, wherein said countercurrent reaction zone comprises a plurality of mixer-settlers in combination with a plurality of columns.

5. The process of claim 4, wherein a plurality of mixer-settlers are used and hydrogen peroxide is fed to each of them, the reaction being continued in a column.

6. The process of claim 3, wherein the organic solvent is selected from the group of organic solvents consisting of halogenated aliphatic hydrocarbons, halogenated cycloaliphatic hydrocarbons and halogenated aromatic hydrocarbons.

7. The process of claim 6, wherein the organic solvent is propylene dichloride.

8. The process of claim 3, wherein the organic solvent is selected from the group of organic solvents consisting of aliphatic hydrocarbons, cycloaliphatic hydrocarbons, aromatic hydrocarbons and alkyl-aryl hydrocarbons.

9. The process of claim 8, wherein the organic solvent is benzene.

* * * * *